US007632283B2

(12) United States Patent
Heldreth

(10) Patent No.: US 7,632,283 B2
(45) Date of Patent: Dec. 15, 2009

(54) MODIFIED SYSTEM AND METHOD FOR INTRAOPERATIVE TENSION ASSESSMENT DURING JOINT ARTHROPLASTY

(75) Inventor: Mark A. Heldreth, Mentone, IN (US)

(73) Assignee: Depuy Products, Inc., Warsaw, IN (US)

( * ) Notice: Subject to any disclaimer, the term of this patent is extended or adjusted under 35 U.S.C. 154(b) by 258 days.

(21) Appl. No.: 10/667,685

(22) Filed: Sep. 22, 2003

(65) Prior Publication Data

US 2004/0064073 A1 Apr. 1, 2004

(51) Int. Cl.
*A61B 17/58* (2006.01)
*A61F 2/00* (2006.01)

(52) U.S. Cl. ..................................... 606/102
(58) Field of Classification Search ............... 606/102; 623/18.11, 20.14, 20.32
See application file for complete search history.

(56) References Cited

U.S. PATENT DOCUMENTS

| | | | |
|---|---|---|---|
| 4,856,993 A | 8/1989 | Maness et al. | |
| 5,033,291 A | 7/1991 | Podoloff et al. | |
| 5,197,488 A | 3/1993 | Kovacevic | |
| 5,213,112 A | 5/1993 | Niwa et al. | |
| 5,326,363 A | 7/1994 | Aikins | |
| 5,360,016 A | 11/1994 | Kovacevic | |
| 5,425,775 A | 6/1995 | Kovacevic et al. | |
| 5,470,354 A | 11/1995 | Hershberger et al. | |
| 5,496,352 A | 3/1996 | Renger | |
| 5,656,785 A | 8/1997 | Trainor et al. | |
| 5,733,292 A * | 3/1998 | Gustilo et al. ............... 606/88 |
| 5,840,047 A | 11/1998 | Stedham | |
| 6,174,294 B1 | 1/2001 | Crabb et al. | |

FOREIGN PATENT DOCUMENTS

| | | |
|---|---|---|
| EP | 0979636 A2 | 2/2000 |
| EP | 0979636 A3 | 2/2000 |
| EP | 1304093 A1 | 4/2003 |
| WO | WO 92/17113 A1 | 10/1992 |
| WO | WO 99/35972 A1 | 7/1999 |
| WO | WO 00/38570 A1 | 7/2000 |
| WO | WO 01/64143 A2 | 9/2001 |

OTHER PUBLICATIONS

European Search Report for European Application No. 03256122.7—2310 PCT, Sep. 8, 2005, 4 pages.
Attfield SF, Warren-Forward M, Wilton T, Sambatakakis A. Measurement of soft tissue imbalance in total knee arthroplasty using electronic instrumentation, Med Eng Phys 1994; 16: 501-5.

(Continued)

*Primary Examiner*—Anu Ramana

(57) ABSTRACT

A modified system for assessing tension intraoperatively during joint arthroplasty includes a discrete sensor array, protector and trial. The protector is mechanically connected to the joint trial and covers the sensor array to protect it from wear. The sensor array can be positively located to prevent it from moving during use. In assembly of the modified system, the sensor array and protector are sterilized as discrete elements. After sterilization, the protector is removably attached to one of the trials with the sensor array substantially covered by the protector to protect the sensor from wear.

21 Claims, 10 Drawing Sheets

OTHER PUBLICATIONS

Attfield SF, Wilton TJ, Pratt DJ, Sambatakakis AS. Soft-tissue balance and recovery of proprioception after total knee replacement. JBJS 1996, 78-B: 540-5.

Briard, Keblish, Buechel. LCS UNI Surgical Technique brochure (0601-00-000), published by DePuy, 1998: pp. 5-6.

Fehring TK, Valadie AL. Knee instability after total knee arthroplasty. Clin Orthop 1994; 299: 157-62.

Gebhard, JS, Kilgus DJ. Dislocation of a posterior stabilized total knee prosthesis: a report of two cases. Clin Orthop 1990; 254-225-9.

Keblish, Jr, MD, Peter. Operative Techniques in Orthopaedics, vol. 8, No. 3 Jul. 1998: pp. 134-145.

Insall, MD, John. Surgery of the Knee, published by Churchill Livingstone, 1984: pp. 626-629.

Lotke PAA, Ecker ML. Influence of positioning of prosthesis in total knee replacement. JBJS 1977; 59A: 77-79.

Moreland JR. Mechanism of failure in total knee arthroplasty. Clin Orthop 1988; 226: 49-64.

Ritter MAAA, Faris PM, Keating EM, Meding JB: Postoperative alignment of total knee replacement. Clin Orthop 1994; 299: 153-6.

Sambatakakis A, Attfield SF, Newton G. Quantification of soft-tissue imbalance in condylar knee arthroplasty. J Biomed Eng 1993, 15: 339-43.

Takahaski T, Wada Y, Yamamoto H. Soft-tissue balancing with pressure distribution during total knee arthroplasty. JBJS 1997, 79-B; 235-39.

Wallance AL, Harris Ml, Walsh WR, Bruce WJM. Intraoperative assessment of tibiofemoral contact stresses in total knee arthroplasty. J Arthroplasty 1998, 13(8): 923-7.

Wasielewski RC, Galante JO, Leighty RM, Natarajan RN, Rosenberg AG. Wear patterns on retrieved polyethylene inserts and their relationship to technical considerations during total knee arthroplasty. Clin Orthop 1994; 299: 31-43.

Carlson, Charles E., et al., "A Radio Telemetry Device for Monitoring Cartilage Surface Pressures in the Human Hip," IEEE Transactions on Biomedical Engineering (Jul. 1974) vol. BME-21, No. 4.

Rydell, Nils W., "Forces Acting on the Femoral Head-Prosthesis," (1966).

Harris, M.L., et al, "An Improved Method for Measuring Tibiofemoral Contact Areas in Total Knee Arthroplasty: A Comparison of K-Scan Sensor and Fuji Film," Journal of Biomechanics (1999), 32 ed., p. 951-958.

Szivek, John A., Phd., et al, "Average and Peak Contact Stress Distribution Evaluation of Total Knee Arthroplasties," The Journal of Arthroplasty (1996), vol. 11 (No. 8), p. 952-963.

Behrens, Fred M.D., et al, "Bendign Stiffness of Unilateral and Bilateral Fixator Frames," Clinical Orthopaedics and Related Research (Sep. 1983), p. 103-110.

Valdevit, Antonio, et al, "Characterization and Application of Think Film Pressure Sensors," Bio-Medical Materials and Engineering (1999), p. 81-88.

Gola, M.M., et al, "Developments in Transducer Stems for Mechanical Coupling Measurements in Endoprosthetics," MEP Ltd. (1982), vol. 11 (No. 4), p. 183-186.

An, Kai-Nan et al, "Direct In Vivo Tendon Force Measurement System," J. Biomechanics (1990), vol. 23 (No. 12), p. 1269-1271.

Filiaggi, Mark J., et al, "Evaluating Sol-Gel Ceramic Thin Films for Metal Implant Applications. II. Adhesion & Fatigue Properties of Zirconia Films on Ti-6A1-4V," Journal of Biomedical Materials Research (Applied Biomaterials) (1996), p. 239-256.

Kaufman, Kenton R., et al, "Instrumented Implant for Measuring Tibiofemoral Forces (1996)," Journal Biomechanics, vol. 29 (No. 5), p. 667-671.

Markolf, Keith L., Ph.D., et al, "In Vitro Measurement of Bone-Acrylic Interface Pressure During Femoral Component Insertion," Clinical Orthopaedics and Related Research (Nov.-Dec. 1976), p. 60-66.

English, T.A., et al, "In Vivo Records of Hip Loads Using a Femoral Implant with Telemetric Output (A Preliminary Report)," Journal Biomedical Engineering (Apr. 1979), vol. 1 (No. 2), p. 111-115.

Oh, Indong, M.D., et al, "Proximal Strain Distribution in the Loaded Femur," The Journal of Bone and Joint Surgery (Jan. 1978), vol. 60A (No. 1), p. 75-85.

Takahashi, Toshiaki et al, "Soft Tissue Blancing with Pressure Distribution During Total Knee Arthroplasty," The Journal of Bone and Joint Surgery (Mar. 1997), p. 235-239.

Davy, D.T., et al, "Telemetric Force Measurements Across the Hip after Total Arthroplasty," The Journal of Bone and Joint Surgery (Jan. 1988), vol. 70A (No. 1), p. 45-50.

Brown, Richard H., et al, "Telemetering In Vivo Loads from Nail Plate Implants," Journal Biomechanics (1982), vol. 15 (No. 11), p. 815-823.

Lau, J.J., et al, "The Influence of Inserting of Fuji Pressure Sensitive Film Between the Tibiofemoral Joint of Knee Prosthesis on Actual Contact Characteristics," Clinical Biomechanics (2001), p. 160-166.

Gupta, Sushi k., M.D., et al, "Use of Piezoelectric Film Sensor for Monitoring Vascular Grafts," The American Journal of Surgery (Aug. 1990), p. 182-186.

McDermott, A.G.P., M.D., et al, "A New Method to Measure Intraosseous Pressures," Clinical Orthopaedics and Related Research (Jul. 1986), p. 25-27.

Mann, R.W., et al, "Rehabilitation Implications of In Vivo Hip Pressure Measurements," Proceedings of the Ninth Annual Conference on Rehabilitation Technology (Jun. 23-26, 1986), Association for the Advancement of Rehabilitation Technology (Minneapolis, Minnesota (Copyright 1986)).

Rushfeldt, P.D., et al, "Improved Techniques for Measuring In Vitro The Geometry and Pressure Distribution in the Human Acctabulum—II. Instrumented Endoprosthesis Measurement of Articular Surface Pressure Distribution," J. Biomechanics, vol. 14 (No. 5), p. 315-323.

Carlson, Charles E., et al, "A Look at the Prosthesis-Cartilage Interface: Design of a Hip Prosthesis Containing Pressure Transducers," J. Biomedical Material Research Symposium (1974), John Wiley & Sons, Inc., p. 261-269.

Hodge, W.A., M.D., et al, "Contact Pressures from an Instrumented Hip Endoprosthesis," The Journal of Bone and Joint Surgery Incorporated (Oct. 1989), vol. 71A (No. 9), p. 1378-1386.

Johnson, Wesley D., et al, "Test Methodology: Evaluation of Load Transfer Across a Total Knee Replacement," Spring National Design Engineering Show & Conference, p. 131-138.

Bereiter, H., M.D., et al, "Telemetric Measurement of the Pressure Conditions in the Interface of an Implanted Acetabulum Prosthesis (In-Vivo)," Rhatisches Kantonsspatal Chur, Institut fur Physik Basel, Orthopadische Universitatsklinik Basel.

Wasielewski, Ray C. "Declaration" unpublished, dated Aug. 22, 2007.

* cited by examiner

MODIFIED SYSTEM AND METHOD FOR INTRAOPERATIVE TENSION ASSESSMENT DURING JOINT ARTHROPLASTY

BACKGROUND OF THE INVENTION.

The present invention relates to a system and method for intraoperative assessment of tension during joint arthroplasty. The system and method of the present invention can be used to perform soft tissue balancing and in selecting implant components.

In total joint replacement or arthroplasty, bone orientation, selection of prosthetic joint components and soft tissue balancing are critical to the success of the procedure. Considering, for example, total knee arthroplasty, one or more cutting jigs are used to ensure that the distal end of the femur and proximal end of the tibia are cut in an orientation that will properly align the patient's bones. After the bones are cut or resected, prosthetic components are fixed to the femur, tibia and patella to define the prosthetic knee joint.

A successful joint replacement or arthroplasty procedure results, in part, from selection of prosthetic joint components that are dimensioned and positioned to closely approximate or replicate the geometry and functional characteristics of a natural, healthy joint. Typically, the component selection process includes a pre-operative analysis of joint images. A valuable intraoperative adjunct to image analysis is the temporary fixation of one or more provisional components to a bone or bones of interest at a stage of the arthroplasty procedure prior to permanent fixation of the prosthetic joint. The provisional components are intended to mimic certain aspects of the permanent prosthetic joint in order for a surgeon to validate measurements and to test or "try-out" several different possible component sizes and configurations. Hence, provisional components are aptly known as "trials."

In total knee arthroplasty, femoral and tibial trials are used to assist a surgeon in assessing the correct bone surfaces for implantation of the femoral and tibial portions of the artificial knee. A surgeon uses a tibial tray trial before fixation of the final implant to determine the tibial implant size, to make the appropriate cuts and reams in the bone, to assess alignment and to ensure correct tibial component thickness prior to implanting the tibial components. The surgeon uses the femoral trial for similar purposes.

Successful knee arthroplasty also requires an analysis of the soft tissue supporting the knee. The knee is held together by a number of ligaments, muscles and tendons. Generally, the surgeon must ensure that these ligaments, muscles and tendons will be properly balanced with the prosthetic elements in place. A properly balanced knee joint will demonstrate balanced ligament tension in both extension and flexion. If the ligaments and tendons around the knee are not properly balanced, the result may be poor performance, localized high stress on the prosthetic components and undesirable wear on the prosthetic components.

Commonly, surgeons assess ligament tension through a subjective process using spacer blocks and mechanical tensioners. If the surgeon senses that either the medial or lateral side is under excess tension, the surgeon relieves the excess tension by releasing a part of either the medial or lateral collateral ligament. However, the surgeon does not necessarily obtain the feedback necessary during ligament release to help assess whether the release is adequate throughout the range of motion as can only be done with the trial in place. In addition, the surgeon must be careful to avoid over-release of the collateral ligaments, since the surgeon cannot undo the release.

In some cases it is preferable to retain the native posterior cruciate ligament. Some prosthetic knees are designed to be used with the posterior cruciate ligament in place along with the prosthetic device. In these procedures, surgeons assess tension in the posterior cruciate ligament with femoral and tibial trials in place on the resected surfaces of the femur and tibia. Too much tension could result in premature wear of the prosthetic components, and too little tension can make the knee unstable. Surgeons generally release some of the fibrous attachments between the posterior cruciate ligament and the tibia until they are satisfied with the degree of tension in the ligament. The current intraoperative posterior cruciate ligament release procedure relies heavily on the surgeon's experience and subjective observations, rather than on objective intraoperative measurement of ligament tension.

Similar concerns, procedures and analyses occur in arthroplasty involving other joints.

SUMMARY OF THE INVENTION

The need for an apparatus, system and method for intraoperative analysis during joint arthroplasty is met in the invention described in the application for United States Patent filed concurrently herewith by Ray C. Wasielewski, M.D., entitled "APPARATUS, SYSTEM AND METHOD FOR INTRAOPERATIVE PERFORMANCE ANALYSIS DURING JOINT ARTHOPLASTY," which is incorporated by reference herein in its entirety. That system provides a first joint trial having an articulating surface, a second joint trial having an articulating surface, a flexible sensor array capable of being shaped to define a curved contour, and a protector having a curved contoured surface and being capable of transmitting pressure to the sensor array. The sensor array of that system is capable of generating a signal in response to pressure. In that system, the sensor array and protector are bonded to each other and to the surface of one of the joint trials; this assembly is sterilized as a unit.

The present invention addresses the desirability of providing an alternative sterilization procedure for the apparatus and system disclosed in that patent application. In addition, the system disclosed in that patent application is for use in knee arthroplasty; the present invention relates to the desirability of providing such a system in other joint arthroplasty procedures as well.

In one aspect, the present invention provides a modified system for balancing soft tissue intraoperatively during joint arthroplasty. The modified system comprises complementary mounting members associated with the protector and one of the trials for temporarily securing the sensor array between the protector and the trial. In the modified system, the sensor array is removable from protector and trial without damaging the sensor array, and the complementary mounting members limit movement of the protector with respect to the associated trial so that the position of the articulating surface of the protector is fixed relative to the articulating surface of the associated trial during use.

In another aspect, the present invention provides a modified system for balancing soft tissue intraoperatively during joint arthroplasty. Mating members are associated with the protector and one of the trials for temporarily fixing the position of at least part of the protector with respect to the trial. In the modified system, the sensor array is between the protector and the trial articulating surface. The sensor array is temporarily in a fixed position between the protector and the trial articulating surface and is free from adhesive.

In another aspect, the present invention provides a modified system for balancing soft tissue intraoperatively during joint arthroplasty. The modified system comprises a stud extending between the protector and one of the trials for temporarily fixing the position of at least part of the protector with respect to the trial.

In another aspect, the present invention provides a modified system for balancing soft tissue intraoperatively during joint arthroplasty. The modified system is characterized in that the sensor array is positively located with respect to at least one of the protector and the associated trial. The sensor array is separable from the associated trial and the protector both before and after use.

In another aspect, the present invention provides a method of sterilizing and assembling a system for balancing soft tissue intraoperatively during joint arthroplasty. In the method, the position of at least a portion of the protector is mechanically fixed with respect to one of the trials with the sensor array in a fixed position and substantially covered by at least part of the protector after the sensor array and the protector have been sterilized.

In another aspect, the present invention provides a method of sterilizing and assembling a system for balancing soft tissue intraoperatively during joint arthroplasty. In the method, the position of the curved contoured surface of the protector is mechanically fixed relative to the articulating surface of one of the trials with the sensor array between the curved contoured surface of the protector and the articulating surface of the trial.

BRIEF DESCRIPTION OF THE DRAWINGS

In the accompanying drawings like reference numbers are used for like parts in all embodiments.

DETAILED DESCRIPTION OF THE ILLUSTRATED EMBODIMENTS

The present invention provides a modified system for intraoperative assessment of tension during joint arthroplasty. This intraoperative assessment provides the surgeon with a valuable tool, providing objective information that the surgeon can use, particularly in performing soft tissue release as part of the arthroplasty procedure. As used herein, "intraoperative assessment of tension", "assess tension intraoperatively" and grammatical variations of these phrases are intended to include the provision of information useful for soft tissue release and balancing as well as the for the selection of implant components, and any other use of such information; these phrases are not intended to exclude other analyses or other uses of this information.

The basic elements of the system disclosed in "APPARATUS, SYSTEM AND METHOD FOR INTRAOPERATIVE PERFORMANCE ANALYSIS DURING JOINT ARTHOPLASTY," filed concurrently herewith by Ray C. Wasielewski, M.D., can be used in the present invention, modified as described below.

The modified system and method of the present invention can be used in knee, hip, wrist, shoulder and ankle joint arthroplasty, for example. Examples of some of such potential uses are illustrated in the accompanying drawings. However, the present invention is not limited to any particular use unless expressly called for in the claims.

In each of the embodiments, the modified system of the present invention includes two joint trials, a first instrumented joint trial generally designated 10A-F in FIGS. 1, 4, 9, 12, 18, 20, 23 and a second joint trial designated 12A and 12 D-F in FIGS. 4, 19, 21 and 22. It should be understood that the second joint trial 12A shown in FIG. 4 can be used with the first joint trials 10A, 10B, 10C of the first three embodiments of the invention.

Figure 1:
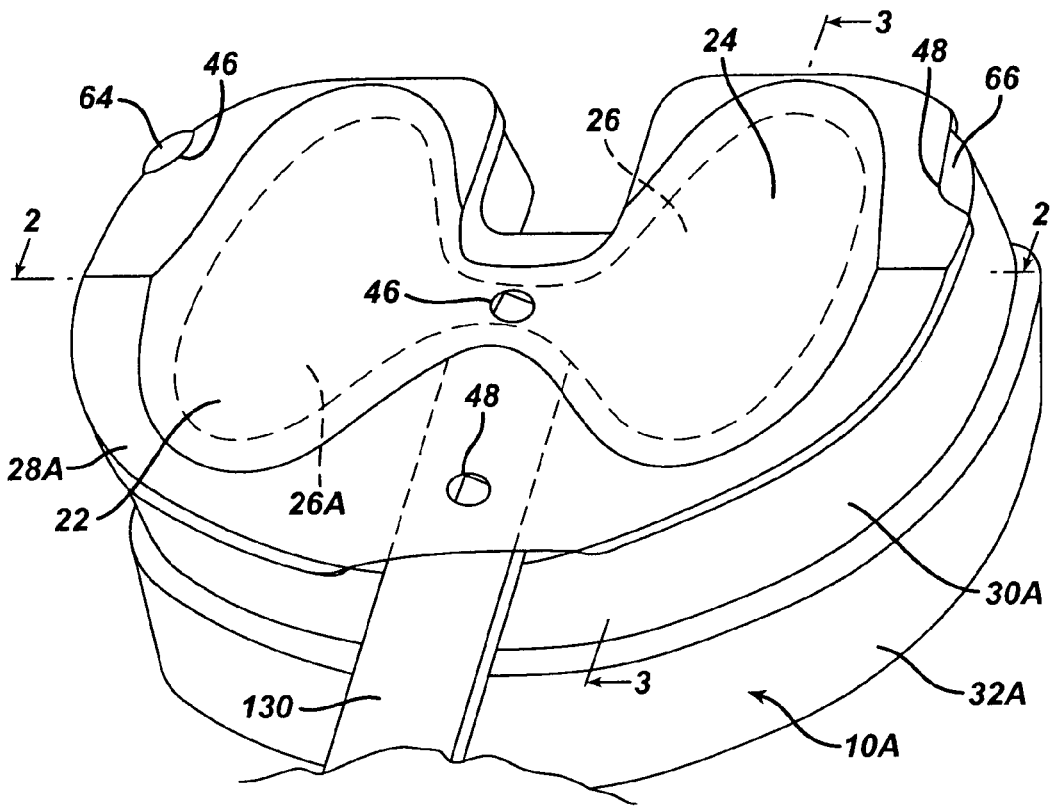
FIG. 1 is a perspective view of an instrumented tibial trial incorporating the principles of the present invention.
Figure 2:
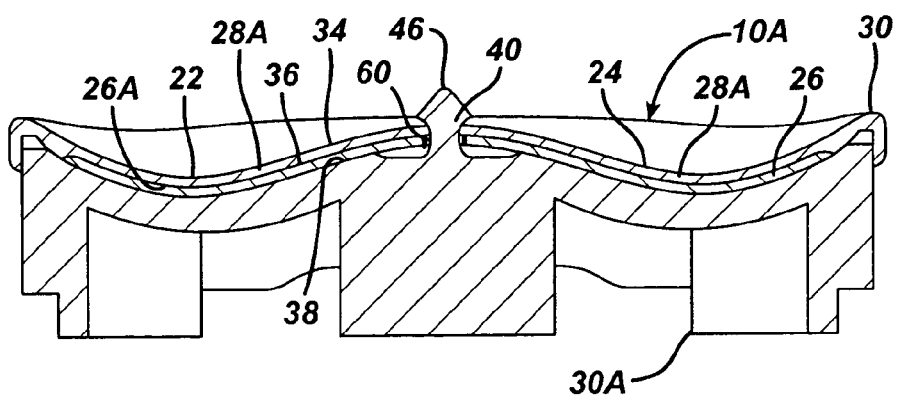
FIG. 2 is a cross-section of the instrumented tibial insert trial portion of the instrumented tibial trial of FIG. 1, taken along line 2-2 of FIG. 1.
Figure 3:
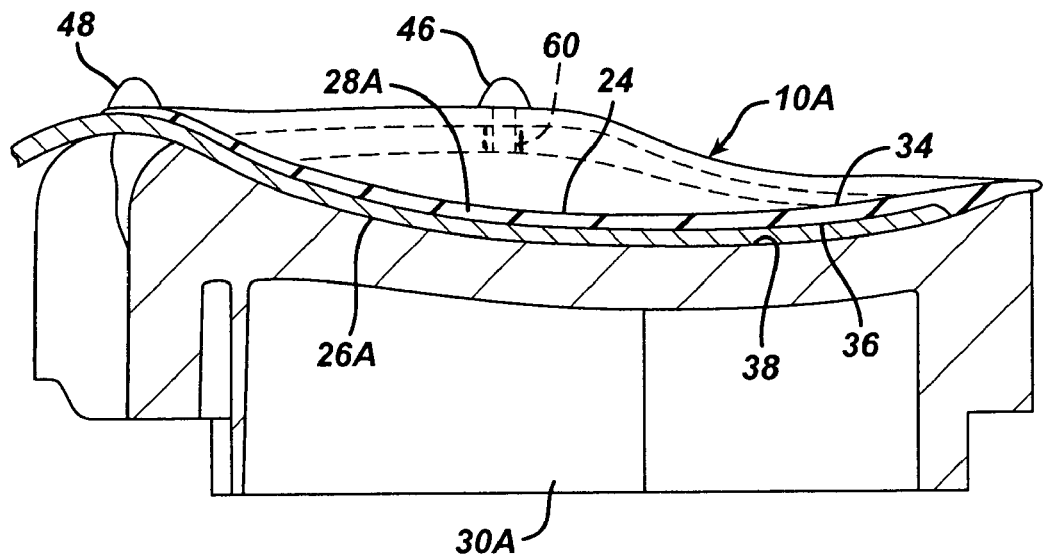
FIG. 3 is a cross-section of the instrumented tibial insert trial portion of the instrumented tibial trial of FIGS. 1-2, taken along line 3-3 of FIG. 1.
Figure 4:
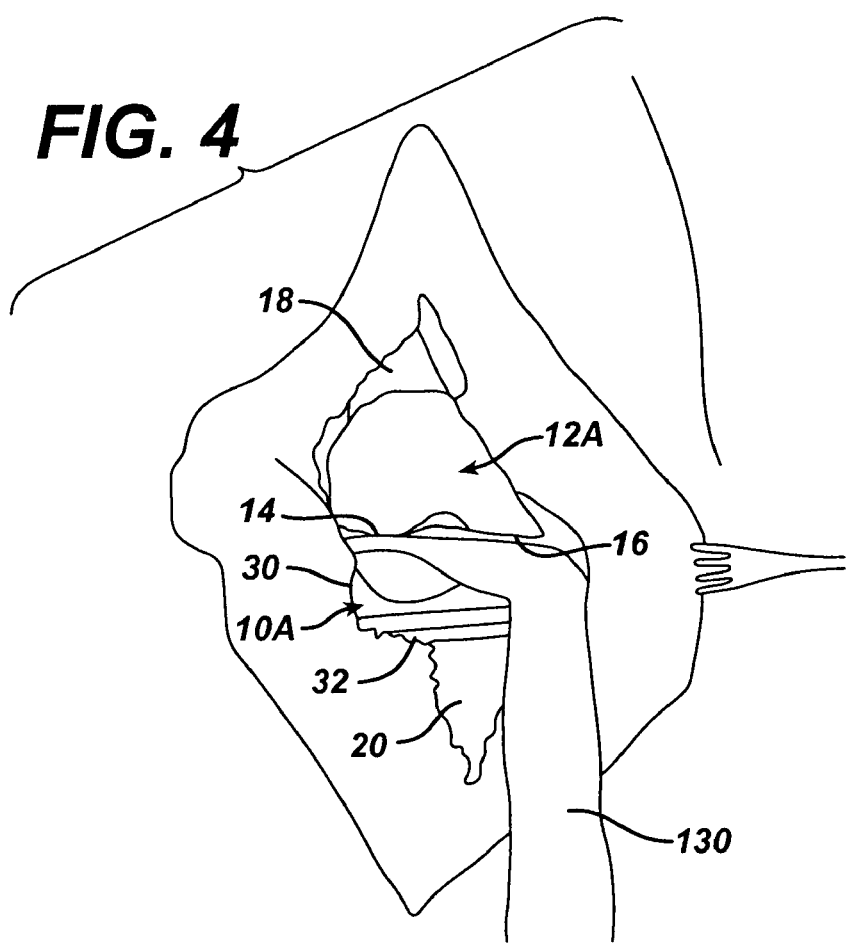
FIG. 4 is a diagrammatic view of the instrumented tibial trial of FIGS. 1-3, together with a femoral trial, in position on the resected tibial and femoral surfaces of a patient.
Figure 9:
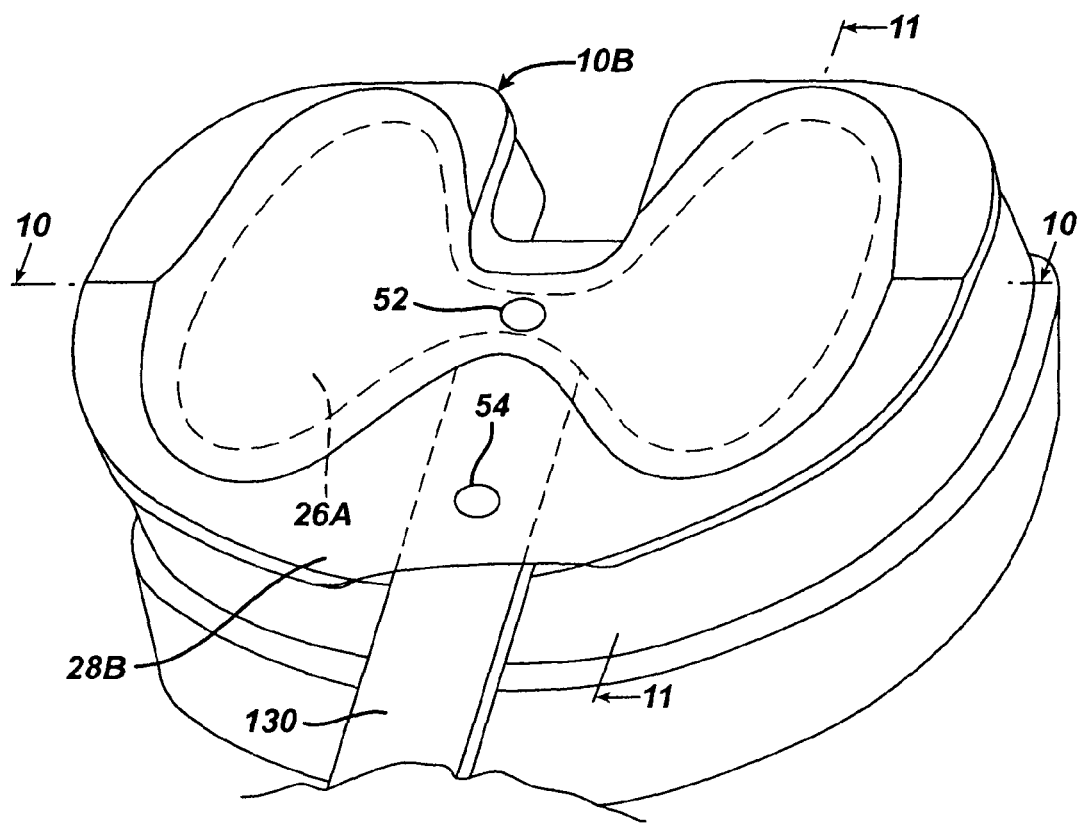
FIG. 9 is a perspective view of a second embodiment of an instrumented tibial trial incorporating the principles of the present invention.
Figure 11:
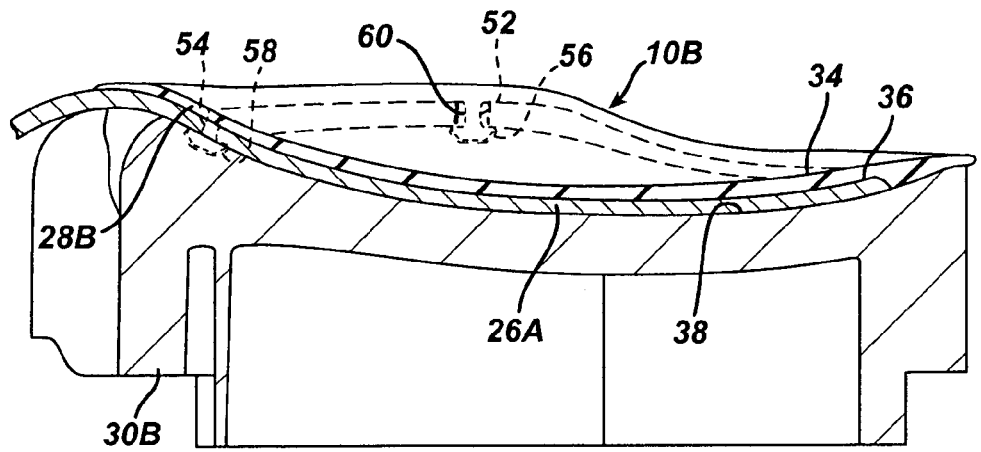
FIG. 11 is a cross-section of the instrumented tibial insert trial portion of the instrumented tibial trial of FIGS. 9-10, taken along line 11-11 of FIG. 9.
Figure 12:
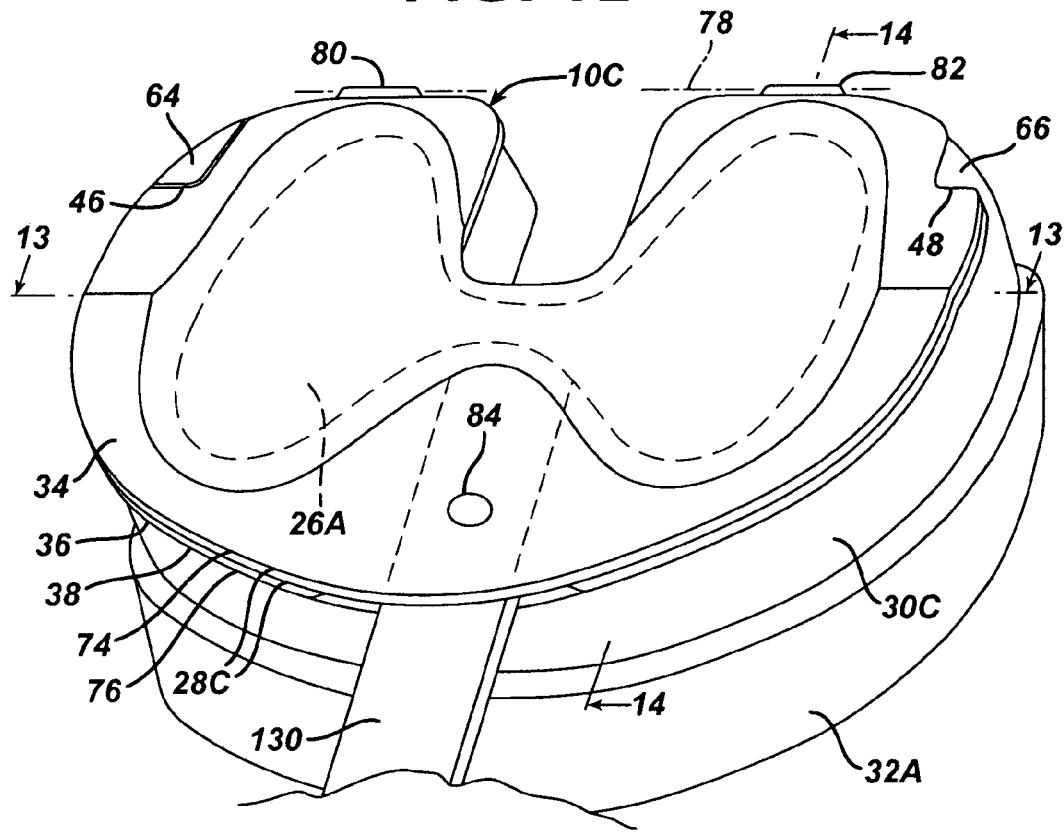
FIG. 12 is a perspective view of a third embodiment of an instrumented tibial trial incorporating the principles of the present invention.

The first three embodiments of the invention, illustrated in FIGS. 1-17, are for use in knee arthroplasty to provide information for assessing tension intraoperatively. In all of these embodiments, the first joint trials 10A, 10B, 10C comprise modified instrumented tibial trial assemblies. These modified instrumented tibial trial assemblies can be used with a femoral trial, shown as 12A in FIG. 4, as disclosed in "APPARATUS, SYSTEM AND METHOD FOR INTRAOPERATIVE PERFORMANCE ANALYSIS DURING JOINT ARTHOP- LASTY." As shown in FIG. 4, the femoral trial has curved convex articulating surfaces 14, 16. The femoral trial is temporarily mounted at the distal end of the femur 18 and the tibial trial 10A is temporarily mounted at the proximal end of the tibia 20. As shown in FIGS. 1, 9 and 12, each of the instrumented tibial trials 10A, 10B and 10C has curved concave articulating surfaces 22, 24; these concave articulating surfaces 22, 24 receive the convex articulating surfaces 14, 16 of the femoral trial 12A. As in the original system, there is a flexible sensor array 26 and a protector 28 in the modified system. However, in this modified system, the sensor array 26 and protector 28 are not bonded together. The sensor array 26 and protector 28 can be supplied to the surgeon as discrete elements in separate packages subjected to separate, and perhaps different, sterilization procedures. The surgeon can then assemble the sensor array 26, protector 28, tibial insert trial 30 and tray trial 32 intraoperatively. After this initial use, the modified system of the present invention allows for separation of the sensor array from the protector so that they can be separately cleaned and sterilized and then prepared for reuse.

In the following description, the designation 26A is used to refer to the flexible sensor array that is sized and shaped for use in knee arthroplasty. The designation 26D is used for the sensor array that is sized and shaped for use in hip arthroplasty. The designation 26E is used for the sensor array that is sized and shaped for use in shoulder arthroplasty. The designation 26F is used for the sensor array that is sized and shaped for use in wrist arthroplasty. Otherwise, each of these sensor arrays 26A, 26D-F may have similar characteristics as described below.

Designations 28A-28G are used for the various designs illustrated for protectors, and designations 30A-30F are used for the various designs of trials that are later assembled into instrumented trials, designated 10A-10F in the drawings. Designations 32A, 32D-F are used for the various elements that receive the trial elements 30A-30F.

The femoral trial 12A and tibial tray trial 32A of the modified system can be standard commercially available trials, such as those available from DePuy Orthopaedics, Inc. of Warsaw, Ind. Suitable standard prosthetic femoral and tibial tray trials are available from DePuy under trademarks such as LCS®, LCS® COMPLETE, P.F.C.® SIGMA, and P.F.C.® SIGMA RP™. However, it should be understood that these commercial products are identified for purposes of illustration only; the invention is not limited to any particular product unless expressly called for in the claims. The tibial insert trials 30A-30C may have many of the standard features of the corresponding commercially available tibial insert trials 30A-30C, modified as described below.

The designs, shapes, sizes and construction of the femoral and tibial trial elements may vary from those illustrated. Other implant designs will typically have trials and trial components generally corresponding in shape and size to the implant components. For example, the present invention may be applied to trials for use with cruciate retaining prosthetics as well as posterior stabilized prosthetics, whether fixed or mobile bearing.

Each of the sensor arrays 26A, 26D-F in the illustrated embodiments comprises a grid of pressure transducers connected together to define a thin, flexible and conformable sheet. For the knee system, two sensor arrays can be provided, one for each of the medial and lateral curved concave portions of the articulating surface of the tibial insert trial. Alternatively, a butterfly-shaped sensor array could be provided, one wing for each of the medial and lateral curved concave portions of the articulating surface. Such butterfly-shaped sensor arrays 26A are shown in the illustrated embodiments of knee systems. The pressure transducers of the sensor arrays produce a signal in response to pressure; in the illustrated embodiment the pressure transducers produce electrical signals, but the invention is not so limited unless expressly called for in the claims.

An illustrative sensor array 26A, 26D-F preferably has the following characteristics: it is thin (e.g., about 1 mm thick or less), usable over the range of anticipated pressures (e.g., 5-200 N/cm$^2$), elastically deformable to the contour of the trial articulating surface, and is capable of being sterilized, particularly by conventional sterilization techniques. The sensor array or components of the sensor array preferably correspond in shape with the entire articulating surface 22, 24 that is designed to bear against the opposing articulating surface or surfaces 14, 16 of the opposite trial 12A. It should be understood that the actual shape and dimensions for each sensor array can therefore vary with the design and size of the trials and with the particular joint.

A suitable example of a commercially available sensor array 26A, 26D-F is available from novel Electronics Inc. of St. Paul, Minn. (and novel gmbH of Munich, Germany, www.novel.de). It is identified by novel as part of the "pliance" system. Each pad has 128 pressure sensors, a thickness of less than 1 mm, a total sensor area of 43×21.5 mm$^2$, an elasticity of greater than 2%, a sensitivity of less than 2 N/cm$^2$ and greater than 4 N/cm$^2$, and a usable pressure range of 5-140 N/cm$^2$. Two such pads may be used for the tibial trial. It should be understood that this particular sensor array and the above-identified characteristics of the sensor array are provided by way of example only; the present invention is not limited to this sensor array or these characteristics unless expressly called for in the claims. For example, it is expected that new materials and new products will become commercially available that could be used with the present invention; for example, a capacitive fabric could be usable. Moreover, it may be desirable to use separate sensor elements or arrays that are connected to provide input to the same computer. The term "sensor array" as used herein should be understood to include both integral and separate configurations of sensors and sensor mats unless expressly limited by the claims. "Sensor array" is intended to broadly encompass devices such as those described herein as well as those made of other materials (e.g., a capacitive fabric) and having other characteristics.

The protectors 28A-28G in the present invention comprise a formed polymer cover or shell. The protectors for the first three illustrated embodiments of the invention are designated 28A, 28B and 28C, and the protectors for the other embodiments are designated 28D-F.

As in "APPARATUS, SYSTEM AND METHOD FOR INTRAOPERATIVE PERFORMANCE ANALYSIS DURING JOINT ARTHOPLASTY," the protector 28A, 28B, 28C for the knee trials is formed to have medial and lateral curved contours, concave on the proximal side 34 and convex on the side 36 that faces the tibial insert trial 30 to substantially complement the concave contour of the proximal surface 38 of the tibial trial insert.

Generally, the protector 28A-28G is provided to protect the sensor array 26A, 26D-F from the stresses of the trialing process. It should be capable of being sterilized for use in surgery, and should be capable of transferring stress to the sensor array 26A, 26D-F so that forces and pressure distributions and concentrations can be analyzed or evaluated and used as discussed below. The protector 28A-28G in the illustrated embodiments comprises high density polyethylene (HDPE). The illustrated protectors 28A-28F each have a thickness of about 1/32 inch (about 0.8 mm), or slightly more, and each can be formed from a sheet of high density polyethylene. A commercially available material can be used for the protector. Suitable examples include 0.20" HDPE sheet and 0.030" HDPE sheet available from Eastech Plastics of Columbus, Ohio. It should be understood that the particular material and form of this material are identified for purposes of illustration only; the present invention is not limited to any particular polymer or any particular form of polymer unless expressly called for in the claims. For example, depending on the procedure used for making the protector, material such as low density polyethylene and polypropylene might be usable.

Figure 5:
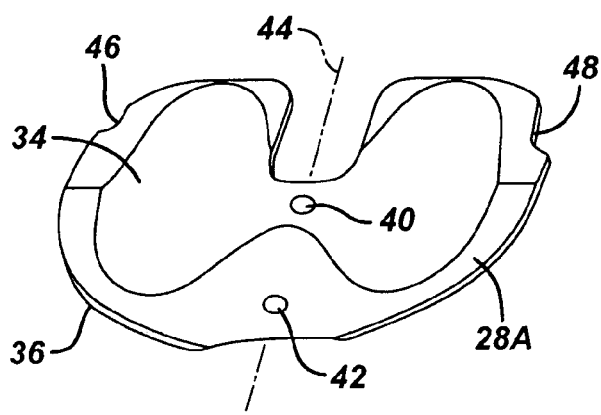
FIG. 5 is a perspective view of the protector of the first embodiment of the instrumented tibial trial.

In the embodiment of FIGS. 1-8, the protector 28A has a plurality of apertures or holes 40, 42 aligned along the central plane 44 of the protector 28A, as shown in FIG. 5. As shown in FIGS. 1 and 5, the first illustrated protector 28A also has a pair of spaced cut-outs 46, 48 along the periphery. The first illustrated tibial trial insert 30A has complementary structures that allow the protector 28A and sensor array 26A to be removably mounted to the tibial trial and to be properly positioned with respect to the tibial trial.

Figure 7:
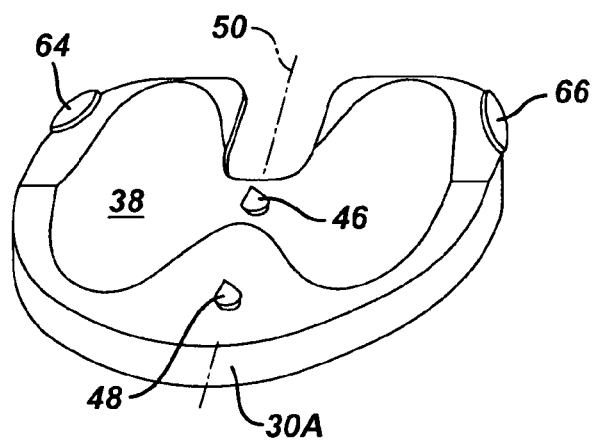
FIG. 7 is a perspective view of the tibial insert trial of the first embodiment of the instrumented tibial trial.
Figure 8:
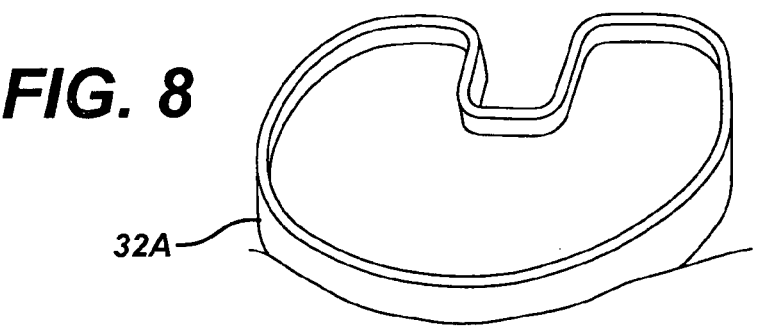
FIG. 8 is a perspective view of a standard tibial tray trial for use with the first embodiment of the invention.

In the first embodiment, as shown in FIG. 7, the tibial insert trial 30A has a pair of upstanding studs 46, 48 integral with the inset trial 30A and extending up from the proximal surface 38 of the trial. The studs 46, 48 are positioned along the central plane 50 of the insert trial 30A to align with the holes 40, 42 of the protector 28A. The studs 46, 48 and holes 40, 42 are complementary to allow for a press-fit or snap-fit of the protector 28A onto the tibial insert trial 30A, and to allow the protector 28A to be manually removed from the tibial insert trial 30A after use.

Figure 10:
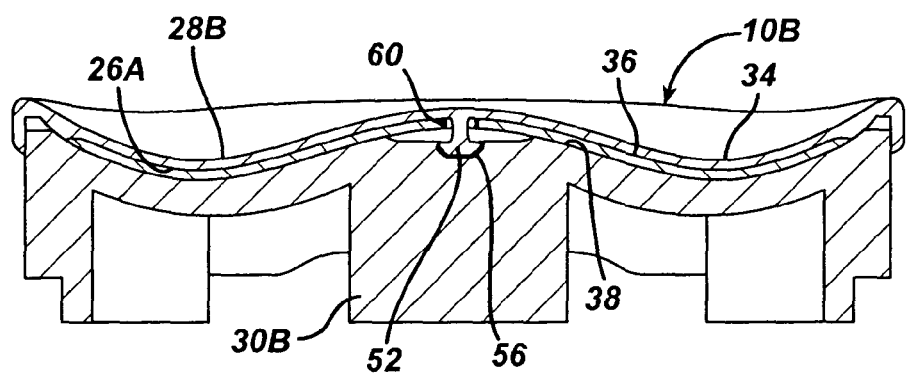
FIG. 10 is a cross-section of the instrumented tibial insert trial portion of the instrumented tibial trial of FIG. 9, taken along line 10-10 of FIG. 9.

It should be understood that variations in this design are possible. For example, as shown in the embodiment of FIGS. 9-11, studs 52, 54 could be formed integral with the protector 28B and could mate with apertures or holes 56, 58 in the insert trial 30B. Although not illustrated, it should be understood that further variations could be made. For example, holes could be provided in both the protector and the insert trial articulating surface, and discrete studs could be inserted to mount the protector on the trial. Studs could also be formed as discrete elements and then bonded to either the protector or the trial. Instead of studs and holes, complementary detents and ledges (as in the embodiment illustrated in FIG. 23 for a trial for a wrist prosthesis), complementary snap elements, or flaps and undercuts, for example, could be formed in the protector and trial to allow for a press-fit or snap-fit mounting of the protector on the trial. Moreover, to simplify mounting and removal of the protector, there could be slits provided in the protector or tibial insert trial around the apertures or holes. Various combinations of the above-mentioned elements could also be employed. However, it should be understood that the invention is not limited to such complementary press-fit or snap-fit structures unless expressly called for in the claims. Structures such as nuts and bolts, screws and clamps could also be used, for example. All of the above-mentioned structures and their equivalents are intended to be encompassed within the phrase "means for mechanically connecting the protector to the trial."

The illustrated complementary mounting members 40, 42 46, 48, 52, 54, 56, 58 serve to limit movement of the protectors 28A, 28B away from the proximal articulating surface 38 of the trial insert 30A, 30B, and provide a predetermined maximum distance between the articulating surface 38 of the trial insert 30A, 30B and the articulating surface 34 of the protector 30A, 30B. Since the sensor array 26A is placed between the protector 28A, 28B and the articulating surface 38 of the trial insert 30A, 30B, this predetermined maximum distance corresponds generally with the sum of the thickness of the protector 28A, 28B and the thickness of the sensor array 26A. Thus, the combination of the shape of the protector 28A, 28B and the mounting mechanism also lock the sensor array 26A between complementary concave and convex surfaces, and force the flexible sensor array 26A to generally conform to the shape of the insert trial articulating surface 38. Thus, when the elements 26A, 28A or 28B, 30A or 30B are assembled, the sensor array 26A will have a curved contour like those of the proximal articulating surface 38 of the insert trial 30A, 30B and the protector 28A, 28B. Similar results are obtained with the other sensor arrays 26D-F and protectors 28C-28F.

In the first two illustrated embodiments, the sensor array 26A has preformed holes 60, 62 corresponding to the positions of the preformed holes in the protector or insert trial, and the studs extend through the holes 60, 62 in the sensor array 26.

Figure 6:
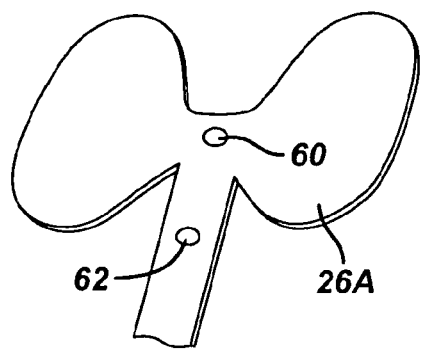
FIG. 6 is a perspective view of the sensor array of the first embodiment of the instrumented tibial trial.

The first illustrated embodiment also includes locating features. As shown in FIGS. 6-7, the protector 28A has a pair of cut-outs 46, 48 and the proximal surface 38 of the insert trial 30A has a pair of mating lands 64, 66. The fit of the cut outs 46, 48 and the lands 64, 66 assures proper positioning of the protector 28A on the insert trial 30A. It should be understood that other locating features can be used, generally including any set of complementary structures on the trial and protector.

In the illustrated embodiments, the studs 46, 48, 52, 54 and lands 64, 66 are positioned so that they are spaced from areas of the tibial insert trial 30A that will be in contact with the convex condyles 14, 16 of the femoral trial 12A. Thus, the studs and lands do not interfere with normal use and operation of the trials.

Figure 15:
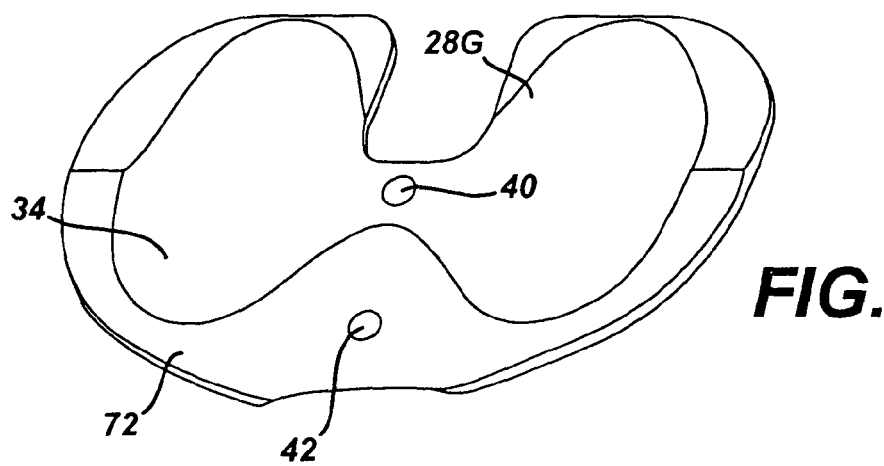
FIG. 15 is a perspective view of an alternate embodiment of a protector for use as part of a modified instrumented tibial trial.
Figure 16:
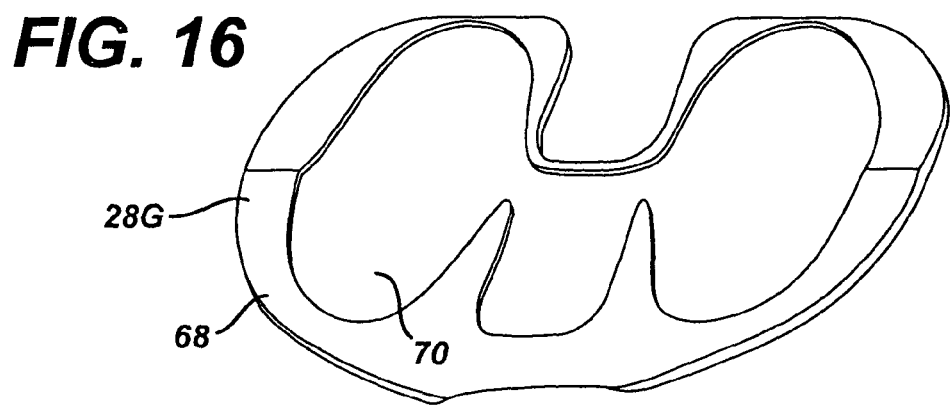
FIG. 16 is a perspective view of a positioner for use as part of a modified instrumented tibial trial.
Figure 17:
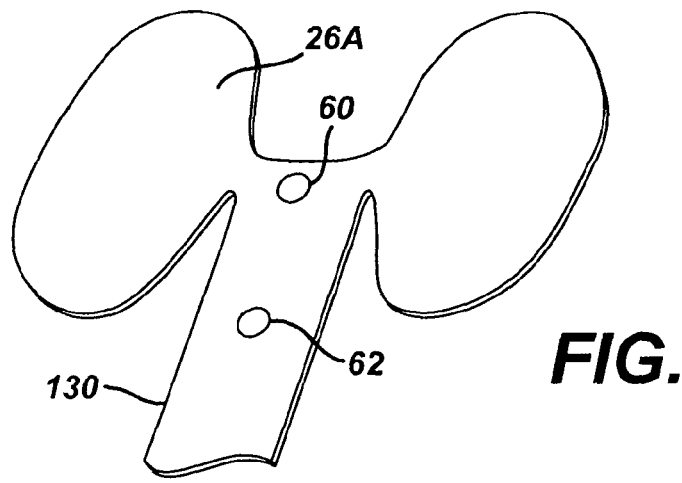
FIG. 17 is a perspective view of a sensor array for use with the protector and positioner of FIGS. 15-16.

In addition, if it is desired to positively locate the sensor array 26A relative to the insert trial articulating surface 38 or the facing surface 36 of the protector 28A, 28B, sensor array locating structures could be formed or otherwise provided on the insert trial or on the protector. For example, a depression corresponding in shape to the shape of the sensor array 26A could be formed on the distal or facing surface 36 of the protector 28 or on the proximal surface of the tibial insert trial 30A, 30B to positively locate the sensor array. Alternatively, as shown in FIGS. 15-17, a two layer protector 28G could be employed: a distal layer 68 could have a cut-out 70 shaped to correspond to the shape of the sensor array 26A, and a proximal layer 72 could be shaped and constructed substantially like the protectors 28A, 28B of one of the preceding embodiments. The two layers 68, 72 and sensor array 26A could then be assembled and mounted on an insert trial 30A, 30B like those of the first illustrated embodiments. Similar designs may be employed for the other sensor arrays 26D-F and protectors 28D-F.

Figure 13:
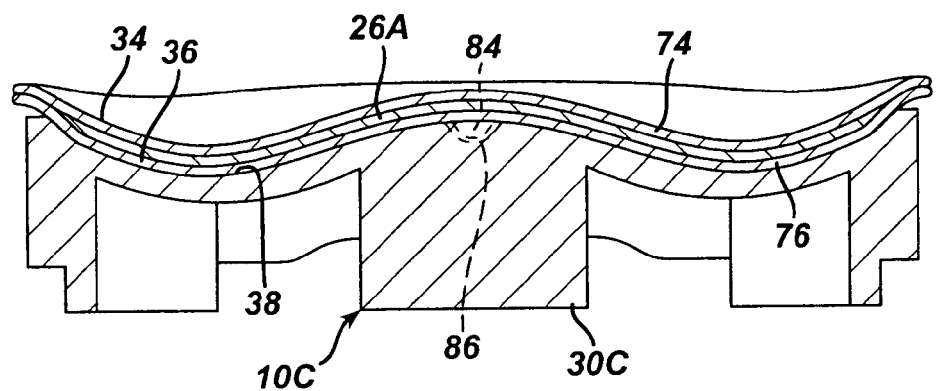
FIG. 13 is a cross-section of the instrumented tibial trial portion of the instrumented tibial trial of FIG. 12, taken along line 13-13 of FIG. 12.
Figure 14:
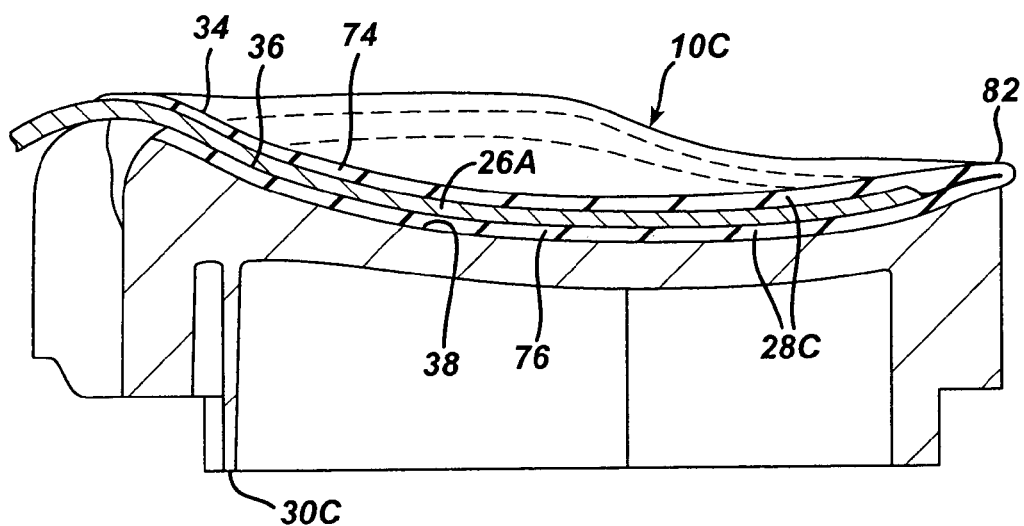
FIG. 14 is a cross-section of the instrumented tibial trial portion of the instrumented tibial trial of FIGS. 12-13, taken along line 14-14 of FIG. 12.

Another alternative embodiment of a protector 28C is shown in FIGS. 12-14. In this embodiment, the protector comprises a first or proximal portion 74 and a second or distal portion 76. The two portions 74, 76 are joined together along an axis 78 through two hinge portions 80, 82 in a clam shell configuration. The two portions 74, 76 are similarly shaped so that the first portion 74 essentially nests in the second portion 76. The distal facing surface of the distal portion 76 has two areas that each have a convex contour to be received in the concave contours of the proximal surface 38 of the insert trial 30C. The proximal surface of the proximal portion 74 has two areas with concave contours to receive the convexly contoured distal surfaces 14, 16 of the femoral trial 12A. In this embodiment, the sensor array 26A is received between the two portions 74, 76 of the protector. In this embodiment, a single distally-extending stud 84 is carried by the proximal portion 74 of the protector 28C; the underlying portion of the sensor array 26A or the electrical leads have an aperture 86 for receiving the stud 84, as does the underlying distal portion 76 of the protector and surface of the tibial insert trial. This alternative protector structure could also be employed in systems designed for use with other joints.

In all of the illustrated embodiments, the instrumented trial defined by the assembly of the insert trial 30A-F, protector 28A-G and sensor array 26A, 26D-F can be disassembled so that at least the sensor array 26A, 26D-F is separate and discrete from the protector 28A-G and insert trial 30A-F. This design allows for reuse of the elements of the system and resterilization of the components 26A, 26D-F, 28A-G, 30A-F by the method most suitable to that component.

Figure 18:
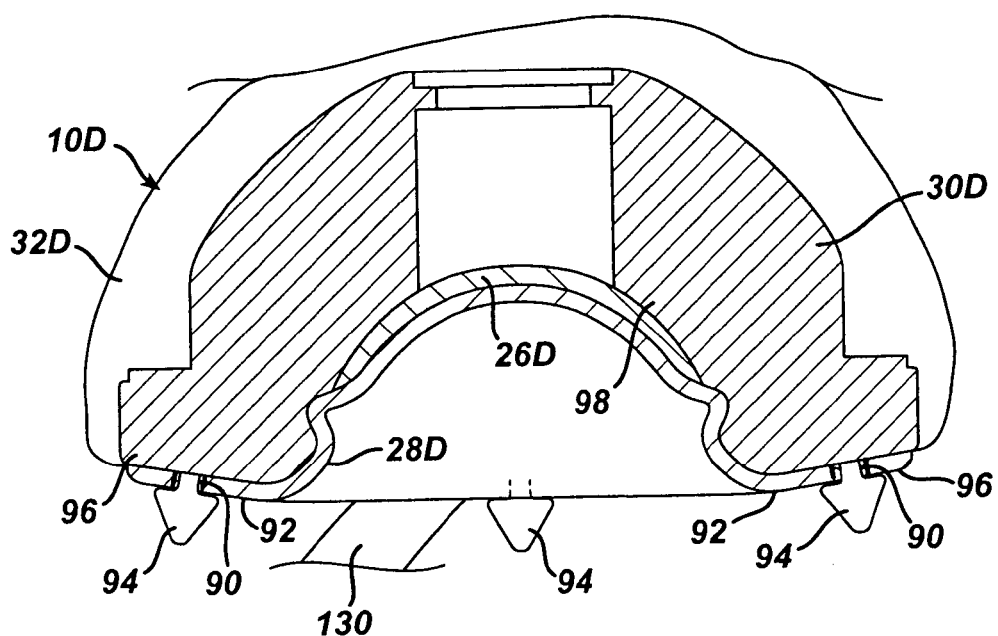
FIG. 18 is a cross-section of an instrumented acetabular liner for use with an acetabular trial.
Figure 19:
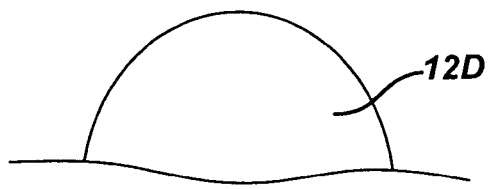
FIG. 19 is a side elevation of a typical femoral head trial for a hip prosthesis trial.

Examples of other potential additional uses of the modified system of the present invention are illustrated in FIGS. 18-23. FIG. 18 illustrates a protector 28D and sensor array 26D removably mounted to the concavely contoured surface an acetabular liner trial 30D that is received in a shell trial 32D. An example of a trial femoral head 12D, with a convexly contoured surface is illustrated in FIG. 19. Together, the instrumented acetabular trial 10D and femoral head 12D comprise a system that allows for intraoperative assessment of tension and for soft tissue balancing during hip joint arthroplasty. In this embodiment, the protector 28D has a plurality of holes 90 around an annular non-articulating surface 92 for mounting the protector 28D and sensor array 26D to studs 94 on the annular non-articulating surface 96 of the trial liner 30D. The sensor array 26D is between the curved contours of the protector 28D and the articulating surface 98 of the liner trial 30D; these complementary contours form the flexible sensor array 26D into a complementary curved shape, as illustrated in FIG. 18. It should be understood that the particular arrangement illustrated in FIG. 18 is provided by way of example only. Variations in mounting mechanisms and in shapes and designs of the protector are possible, as described above for the embodiments for use with the knee trials. As in the prior embodiments, the instrumented trial assembly 10D can be disassembled into discrete elements 26D, 28D, 30D, 32D so that the elements 26D, 28D, 30D, 32D can be sterilized independent of one another. The femoral component 12D of the system can also be independently sterilized. The above-described features could be employed with hip trials available from DePuy Orthopaedics, Inc. of Warsaw, Ind.

Figure 20:
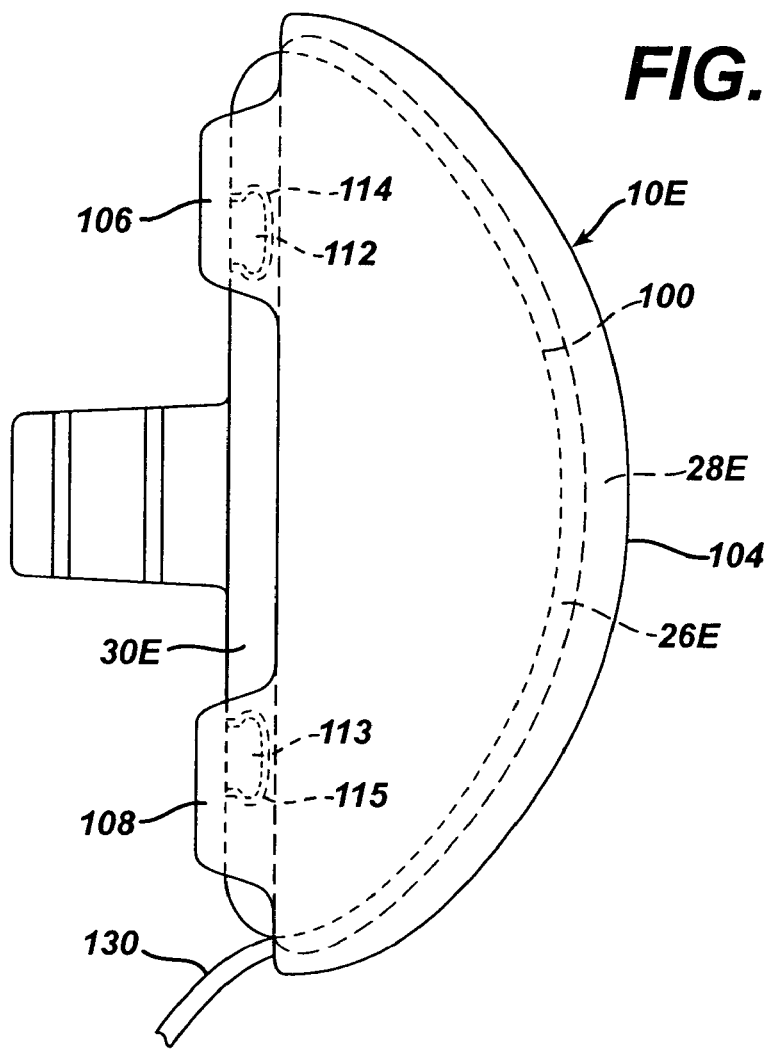
FIG. 20 is a side elevation of an instrumented humeral head trial of a shoulder prosthesis trial.
Figure 21:
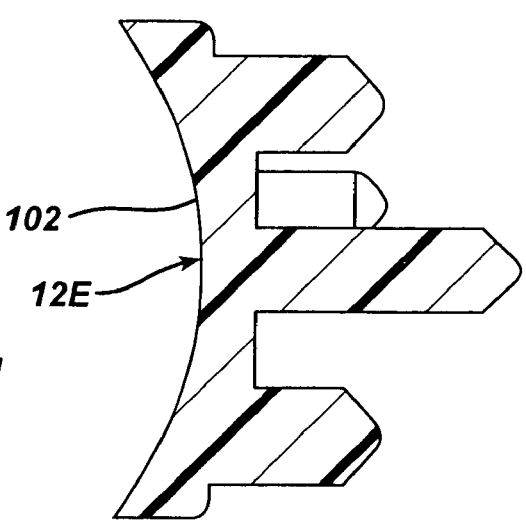
FIG. 21 is a cross-section of a glenoid component trial of a shoulder prosthesis trial.

FIG. 20 illustrates a protector 28E and sensor array 26E removably mounted to the convexly contoured articulating surface 100 of a humeral head trial 30E for use in shoulder arthroplasties. FIG. 21 is a cross-section of a glenoid trial 12E with a concavely contoured articulating surface 102 for receiving the articulating surface 104 of the protector 28E of the instrumented humeral head trial 10E. Together, the first trial 10E and second trial 12E comprise system for assessment of tension and for soft tissue balancing during shoulder joint arthroplasty. In this embodiment, the sensor array 26E and the protector 28E both have convex contours like the articulating surface 100 of the humeral head trial 30E. In the illustrated embodiment, the protector 28E includes a plurality of extensions 106, 108 that fold over the outer edge of the articulating surface 100 and extend over part of the non-articulating surface 110. The portions of the extensions 106, 108 that extend over the non-articulating surface include studs 112, 113 that are received in complementary holes 114, 115 in the humeral head trial 30E to removably mount the combination of the sensor array 26E and the protector 28E to the trial 30E. As in the prior embodiments, the instrumented trial 10E can be disassembled into discrete elements 26E, 28E, 30E so that the elements 26E, 28E, 30E can be sterilized independent of one another. The glenoid component 12E can also be independently sterilized. The above-described features could be employed with shoulder trials available from DePuy Orthopaedics, Inc. of Warsaw, Ind.

Figure 22:
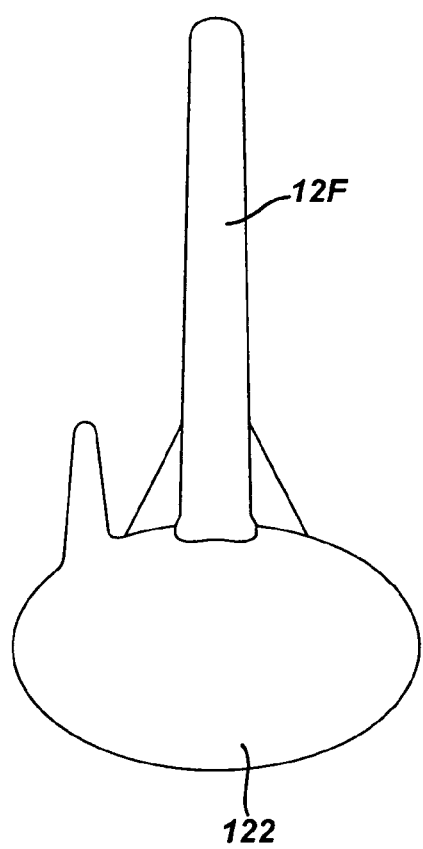
FIG. 22 is a side elevation of a typical metacarpal trial of a wrist prosthesis trial.
Figure 23:
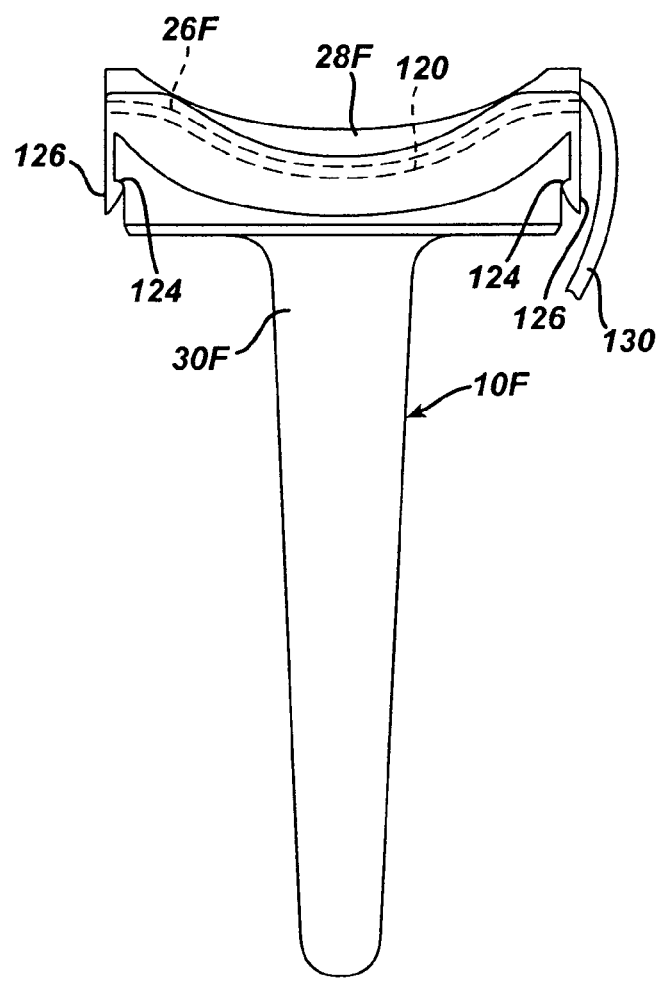
FIG. 23 is a side elevation of an instrumented radial component trial of a wrist prosthesis trial.

FIG. 23 illustrates a protector 28F and sensor array 26F removably mounted to the concavely contoured articulating surface 120 of a radial trial 30F for use in wrist arthroplasties. FIG. 22 illustrates a trial metacarpal component 12F for use in wrist arthroplasty. The metacarpal component 12F has a convexly contoured articulating surface 122. Together, the instrumented trial 10F and second trial 12F comprise a system for assessment of tension and for soft tissue balancing during wrist joint arthroplasty. In the embodiment illustrated in FIG. 23, the trial 30F has undercuts 124 to receive tabs 126 for temporarily mounting the protector 28F and sensor array 26F to the trial 30F. As in some of the prior embodiments, the curvature of the articulating surface 128 of the trial and curvature of the facing surface 130 of the protector 28F form the flexible sensor array 26F into the curved configuration illustrated. And as in the prior embodiments, the instrumented trial 10F can be disassembled into discrete elements 26F, 28F, 30F so that the elements 26F, 28F, 30F can be sterilized independent of one another. The second trial 12F can also be sterilized independent of the components 26F, 28F, 30F of the first trail 10F. The above-described features could be employed with wrist trials available from DePuy Orthopaedics, Inc. of Warsaw, Ind.

Although not illustrated, it should be understood that the principles of the present invention can also be applied to trials used in other joint arthroplasties, such as trials used in implantation procedures for elbow and ankle prosthetics. Trials for other joint arthroplasties that could be modified as described above are available from DePuy Orthopaedics, Inc. of Warsaw, Ind.

For all of the illustrated trials, some variation in the above-described components, system and methods may be desirable. For example, the thickness of the prosthetic trial may be adjusted. Instead of the trial body being dimensioned substantially like the corresponding final implant component, the trial body can be made slightly thinner, to account for the thickness of the protector and sensor array. Thus, the body of the trial 30A-30F can be made 1/32 inch thinner than the implant to account for the thickness of the polymer layer, and can be made an additional 1 mm thinner to account for the thickness of the sensor array; however, it may be desirable for the total insert to be slightly thicker than the reduction in thickness of the trial to insure loading of the insert For all of the illustrated embodiments, the protector 28A-28G may be formed into the illustrated contoured shapes by any appropriate means, such as by machining or molding. For molding the protectors 28A-28G, the base material can be supplied in sheet form and then vacuum molded over the articulating surface of a trial, such as surface 38, 98, 100, 120 of trials 30A, 30B, 30C, 30D, 30E, 30F or can be vacuum molded over a form provided for that purpose. Excess polymer material can be trimmed away. The resultant polymer protector 28A-28G has a curved contour or contours closely approximating the shape of the articulating surface of the trial. For the embodiments of FIGS. 12-14, both layers 74, 76 can be formed in the above manner and then joined together along axis 78 by affixing hinges 80, 82 to the two layers 74, 76 by any appropriate means such as glue or welding. For the embodiment of FIGS. 15-17, the two layers 68, 72 can both be formed by molding such as by vacuum molding.

The material for the protector 28A-28G should be such that the protector retains its shape after the molding operation is complete, and so that the protector is capable of holding its molded shape when mounted on the trial with the flexible sensor array between the protector and the trial.

It may be desirable to mold the protector 28B-28C and 28E-28F around a form that also creates a mounting mechanism such as a stud 52, 54, 84, 112, 113, flap or tab 126, for example, integral with the remainder of the protector 28B-28C and 28E-28F. A form could also be designed so that one or more holes 40, 42, 60, 62 are formed during the molding process for the protectors 28A, 28D and 28G. Alternatively, before or after the molding process is complete, a mounting stud or other mounting member could be bonded to the sheet or formed protector, mechanically connected to the polymer sheet or formed protector or could be supplied to the surgeon as a separate component. Holes can be cut or otherwise formed into the protector or trial at any time during the manufacturing process. Cut-outs such as those shown at 46, 48 can also be formed in any of the illustrated protectors 28A-28G at any point in the manufacturing process, such as by molding them into place or later cutting them out of the formed protector, and lands or other positioning members could also be included and formed as part of the protector or could be made separately and later affixed to the protector.

The trials 30A-30F can be formed in the standard manner. If made of a polymer, they can be molded into the illustrated shapes. For the embodiments including male mounting members such as studs 46, 48, 94 as part of the trial 30A, 30D, the male studs can be formed integral with the trial by molding, by machining them, or by separately forming and then inserting and affixing the studs to the trial. For the embodiments including apertures or holes 56, 86, 114, 115 or undercuts 124 as part of the trial 30B, 30C, 30E, 30F, the holes or undercuts could be formed as part of the trial during the molding process or later machined or otherwise cut into the formed trial.

It should be understood that the above-described manufacturing processes are provided as examples of possible methods for making the components of the instrumented trials 10A-10F of the present invention. The invention is not limited to this or to any other process unless expressly called for in the claims. Other processes may be used. For example, if the polymer protector is formed over a metal base having a top surface shaped like the trial body articulating surface, other forming methods can be used, including methods utilizing higher temperatures.

For each embodiment, the protector 28A-28G, sensor array 26A, 26D-26F and first and second trials 30A-30F, 12A-12F can then be packaged and sterilized as separate units, together as one group, or in sets of elements designated for particular sterilization techniques. The modularity of the modified system of the present invention is advantageous in that independent sterilization is possible, and the sterilization method can be tailored to best fit the element. For example, given the expense of the sensor array, a sterilization method that maximizes the service life of the sensor array can be selected.

Conventional sterilization methods include gas plasma, steam, ethylene oxide, gamma irradiation and chemical disinfection. These methods provide several options for sterilization of the components of the modified system of the present invention. As disclosed in "APPARATUS, SYSTEM AND METHOD FOR INTRAOPERATIVE PERFORMANCE ANALYSIS DURING JOINT ARTHOPLASTY," one example of a suitable system for sterilizing the sensor array is the STERRAD® 100S Sterilization System, a low temperature sterilization system available from Advanced Sterilization Products of Irvine, Calif. The cycle in this commercial system comprises evacuation of the sterilization chamber to 400 mTorr, automatic injection and diffusion of 1.8 ml of vaporized $H_2O_2$ and activation of low temperature $H_2O_2$ gas plasma with 400 W RF power at 500 mTorr pressure for 17 minutes. During the second half of the cycle, the above steps are repeated. The sterilization chamber is then vented to return it to atmospheric pressure.

An additional advantage of providing a modular system as in the present invention is the potential need for fewer sensor arrays. Typical surgical kits include trials of various sizes. It may be desirable to provide fewer sizes of sensor arrays, or a single sensor array, that can be used with several or all of the sizes of trials. The number of protectors provided can correspond with the number of trials provided, or fewer protectors can be provided. Costs can be significantly lowered if fewer sensor arrays, or a single "one size fits all" sensor array is provided.

Assembly of the components of the modified system can be done at the hospital by the surgeon or the surgical staff. The flexible sensor array 26A, 26D-26F may be placed against the articulating surface 38, 98, 100, 120 of the trial 30A-30F and shaped into the illustrated curved contours. The flexible sensor array can also be shaped into the illustrated curved contours be placing it against the facing surface 36 of the protector 28A-28F, or may be placed between the facing surfaces of the layered protectors 28C, 28G of the embodiments of FIGS. 12-17. The flexible sensor array 28A-28F can also be sandwiched between opposing complementary curved surfaces to shape the sensor array into the illustrated curved contours. The protector 28A-28F and sensor array 26A, 26D-26F can then be removably mounted to the trial 30A-30F to lock or fix these elements in place for use and to lock or fix the flexible sensor array 26A, 26D-26F in its contoured shape. The method of removably mounting or fixing the protector and sensor array to the trial will vary with the type of connecting elements used. Generally, for a press-fit or snap-fit connecting system, the stud or tab 46, 48, 52, 84, 94, 112, 113, 126 is pushed or snapped through any hole such as holes 60, 62 in the sensor array, and into the receiving recess or hole 40, 42, 56, 86, 92, 114, 115, 124 temporarily locking the trial 30A-30F, sensor array 26A, 26D-26F and protector 28A-28G together to define an instrumented trial 10A-10F.

The assembled instrumented trials 10A-10F of the present invention can then be used by the surgeon in the manner set forth in "APPARATUS, SYSTEM AND METHOD FOR INTRAOPERATIVE PERFORMANCE ANALYSIS DURING JOINT ARTHOPLASTY."

The surgeon performs the initial surgical steps in the standard manner. When the point of trialing is reached, the surgeon uses the assembled instrumented joint trial 10A-10F of the present invention instead of prior art joint trials, along with a standard complementary prosthetic joint trial 12A, 12D-12F. The electrical connector of the sensor array is hooked up to one end of a lead cord, shown diagrammatically at in 130 FIGS. 1, 4, 9, 12, 17, 18, 20 and 23, the other end of which is hooked up to a computer (not shown). The lead cord 130 can be kept sterile in the field by covering it with a clear tube drape. The system may also include an image recorder (not shown), such as a digital video camera, that is also connected to the computer. The computer may be programmed with commercially available software for analysis of the data provided by the instrumented tibial trial; suitable software is available from novel Electronics gmbH under the designation "pliance" ("pliance FTM-KE" software, along with other components such as a "pliance FTM-KE" electronics analyzer, other novel KE software, etc.).

The surgeon then manipulates the patient's limb, taking the joint through its full range of motion. As the surgeon does so, the articulating surface of one trial contacts the contoured surface of the protector 28A-28G that is mounted on the other trial. Depending on the gap between the resected bones and the size of trials used and the condition of the soft tissue around the joint, there will be forces between the articulating surfaces of the trials. These forces may vary in concentration, position and magnitude with, for example, the position of the joint. The surgeon may concurrently analyze the pressure distribution in areas of the trials to ensure that pressure is not unduly concentrated in one area, to thereby maximize the longevity of the implant.

From the forces measured and pressure distributions, the surgeon can also determine whether additional bone must be removed, whether soft tissue needs to be released, and whether the size of implant is optimal, for example. A series of small soft tissue releases can be performed, and the surgeon can analyze the effect of each to ensure that the release is not excessive. Data from the sensor array can be recorded simultaneously with video images, so that the surgeon is not limited to "real time" evaluation, but can also review the data after manipulating the joint.

The surgeon may wish to use the assembled instrumented trials of the present invention in conjunction with standard surgical tensors, particularly those that measure force mechanically. Thus, the output from the sensor array can be calibrated to correlate with the mechanical measurement. The surgeon may also wish to use the prosthetic trials of the present invention together with spacer blocks.

The display at the computer may include, for example, a video image, a display of the magnitude of force, and a display of the concentration of pressure. As indicated above, the data can be recorded so that the surgeon is not limited to real time analysis. It should be understood that these displays are identified by way of example only; the present invention is not limited to any particular display or to the use of a computer with such inputs unless expressly called for in the claims.

In cruciate retaining knee arthroplasty procedures, the surgeon can use the information provided to release the posterior cruciate ligament. The surgeon can balance the posterior cruciate ligament with the trials in place, and can assess balance using objective data.

After the surgeon is satisfied with the flexion and extension gaps, the size and components of the prosthetic implant trial and the balance of forces exerted by the soft tissue surrounding the joint, the surgeon can then select the optimal prosthetic implant components and continue with the surgery in the normal manner.

The surgeon or surgical team can later disassemble the instrumented trial by removing the protector 28A-28G from the trial 30A-30F, such as by pulling the studs out of the complementary holes. When the protector 28A-28G is removed, the flexible sensor array 26A, 26D-26F is released. The individual elements of the system can then be re-sterilized separately by whatever technique is selected and then reused by assembling an instrumented trial from the re-sterilized elements. Although it may not be desirable to re-sterilize all of the elements, given the cost of the sensor array, it is desirable to re-use the sensor arrays.

It will be appreciated that the principles of the present invention can also be applied to the training of surgeons. For example, the system and method of the present invention could be used in learning surgical techniques on cadavers. The system of the present invention may also prove useful in optimizing the designs of implants.

Although the illustrated embodiments of the invention are associated with one trial for each of the joints, such as tibial trials in the embodiments of FIGS. 1-17, it should be understood that the other trial, such as the femoral trial, could alternatively or additionally be the instrumented one.

While only specific embodiments of the invention have been described and shown, it is apparent that various alternatives and modifications can be made thereto. Moreover, those skilled in the art will also recognize that certain additions can be made to these embodiments. It is, therefore, the intention in the appended claims to cover all such alternatives, modifications and additions as may fall within the true scope of the invention.

It should also be understood that regardless of the form of the following claims, no portion of the preambles of the claims are admitted to be prior art.

I claim:

1. A modified system for balancing soft tissue intraoperatively during joint arthroplasty, the system being of the type having a first joint trial having an articulating surface having a curved contour, a second joint trial having an articulating surface having a curved contour, the curved contour of the articulating surface of the first joint trial being shaped to receive the articulating surface of the second joint trial, a flexible sensor array capable of being shaped to define a curved contour, the sensor array being capable of generating a signal in response to pressure, and a protector having a surface that has a concave curved contour and an opposite surface that has a convex curved contour, the protector being capable of transmitting pressure to the sensor array, the protector having a thickness between the surface with the concave curved contour and the surface with the convex curved contour, the curved contours of the articulating surface of the first joint trial and the curved contoured surfaces of the protector being curved in a plurality of intersecting cross-sections, the modified system comprising:

complementary mounting members associated with the protector and the first joint trial for temporarily securing the sensor array between the protector and the first joint trial, the complementary mounting members being sized, shaped and positioned so that the protector and the sensor array may be temporarily secured on the curved contour of the articulating surface of the first joint trial with the sensor array positioned between the curved contours of the articulating surface of the first joint trial and the curved contoured opposite surface of the protector;

wherein the sensor array is removable from protector and first joint trial without damaging the sensor array; and wherein the complementary mounting members limit movement of the protector with respect to the first joint trial in use so that the position of the protector is fixed relative to the articulating surface of the first joint trial during use.

2. The modified system of claim 1 wherein the complementary mounting members comprise a stud and an aperture.

3. The modified system of claim 1 wherein the complementary mounting members are sized, shaped and positioned to allow the first joint trial and protector to be snap fit together to temporarily combine the protector, sensor array and first joint trial into an assembly for use.

4. The modified system of claim 1 wherein the articulating surface of the first joint trial is concave and the articulating surface of the second joint trial is convex and wherein the complementary mounting members are spaced from the articulating surface of the first joint trial and the articulating surface of the protector.

5. The modified system of claim 4 wherein the first joint trial includes an additional surface adjacent to the concave articulating surface of the first joint trial and wherein one of the complementary mounting members is associated with the additional surface of the first joint trial.

6. The modified system of claim 5 wherein the first joint trial includes a second concave articulating surface and the additional surface adjacent to the concave articulating surface is between the two articulating surfaces of the first joint trial.

7. The modified system of claim 1 wherein the articulating surfaces of the first joint trial and the protector are convex and the articulating surface of the second joint trial is concave and wherein the complementary mounting members are spaced from the articulating surfaces of the first joint trial and the articulating surface of the protector.

8. The modified system of claim 7 wherein the first joint trial has a periphery and the protector has a periphery and the complementary mounting members are associated with the peripheries of the first joint trial and the protector.

9. A modified system for balancing soft tissue intraoperatively during joint arthroplasty, the system being of the type having a first joint trial having an articulating surface having a curved contour, a second joint trial having an articulating surface, a flexible sensor array capable of being shaped to define a curved contour, the sensor array being capable of generating a signal in response to pressure, and a protector having a curved contoured articulating surface and being capable of transmitting pressure to the sensor array, the modified system comprising:
   complementary mounting members associated with the protector and one of the trials for temporarily securing the sensor array between the protector and the trial, the complementary mounting members being positioned so that the protector and the sensor array may be temporarily secured on the curved contour of the articulating surface of the trial;
   wherein the sensor array is removable from protector and trial without damaging the sensor array; and
   wherein the complementary mounting members limit movement of the protector with respect to the associated trial in use so that the position of the articulating surface of the protector is fixed relative to the articulating surface of the associated trial during use; and
   wherein the protector comprises a first portion and a second portion joined along an axis, and wherein the first portion of the protector overlies at least a part of the curved contour of the articulating surface of the first trial and the second portion overlies at least a substantial part of the sensor array and at least a substantial part of the first portion of the protector.

10. A modified system for balancing soft tissue intraoperatively during joint arthroplasty, the system being of the type having a first joint trial having an articulating surface with a curved concave contour and a surface adjacent to the curved concave articulating surface, a second joint trial having an articulating surface with a curved convex contour, a flexible sensor array shaped to define a curved concave contour, the sensor array being capable of generating a signal in response to pressure, and a protector having a surface with a curved concave contour and a surface with a curved convex contour and being capable of transmitting pressure to the sensor array, the curved convex surface of the protector overlying and contacting at least a substantial part of the curved concave contour of the flexible sensor array, the curved concave surface of the protector being exposed above the sensor, the flexible sensor array, the articulating surface of the first joint trial, the curved concave surface of the protector and the curved convex surface of the protector being curved in a plurality of intersecting cross-sections, the modified system comprising:
   a stud extending between the protector and the surface adjacent the curved concave articulating surface of the first joint trial for temporarily fixing the position of at least part of the protector with respect to the trial.

11. A modified system for balancing soft tissue intraoperatively during joint arthroplasty, the system being of the type including a first joint trial having an articulating surface having a curved contour, a second joint trial having an articulating surface, a flexible sensor array associated with one of the trials and being shaped to define a curved contour, the sensor array being capable of generating a signal in response to pressure, and a protector having a curved contoured surface and being capable of transmitting pressure to the sensor array, the sensor array being positioned between the curved contour of the articulating surface of the first joint trial and the curved contoured surface of the protector, the modified system characterized in that:
   the sensor array is positively located with respect to at least one of the protector and the first trial; and
   the sensor array is separable from the associated trial and the protector both before and after use;
   wherein the protector has a first portion and a second portion joined along an axis, wherein the first portion of the protector overlies at least part of the curved contour of the articulating surface of the first trial and the second portion overlies at least a substantial part of the sensor array and a substantial part of the first portion of the protector.

12. A modified system for balancing soft tissue intraoperatively during joint arthroplasty, the system being of the type including a first joint trial having an articulating surface having a curved contour, a second joint trial having an articulating surface having a curved contour, a flexible sensor array associated with one of the trials and having a portion shaped to define a curved contour, the sensor array being capable of generating a signal in response to pressure, and a protector having a surface with a curved concave contour and a surface with a curved convex contour and being capable of transmitting pressure to the sensor array, the protector having a thickness between the curved concave contour and the curved convex contour, the thickness of the protector at the curved contoured surfaces being less than half the thickness of the first joint trial at the articulating surface, the sensor array being positioned between the curved contour of the articulating surface of the first joint trial and the curved contoured surfaces of the protector, the curved contour of the articulating surface of the first joint trial and the curved contoured surfaces of the protector being curved in a plurality of intersecting cross-sections, the modified system characterized in that:
   positive locating features are provided so that the sensor array is positively located with respect to at least one of the protector and the first trial; and
   the sensor array is separable from the associated trial and the protector both before and after use;
   wherein the positive locating features include at least one positive locating feature spaced from the curved contour of the articulating surface of the first joint trial.

13. The modified system of claim 12 wherein the protector and at least one of the joint trials have complementary mounting members.

14. The modified system of claim 13 wherein the complementary mounting members comprise a recess and a protrusion.

15. The modified system of claim 13 wherein the complementary mounting members comprise an aperture and a stud so that the protector can be snap fit to the trial.

16. The modified system of claim 12 wherein the protector is capable of being snap fit to one of the first joint trial to temporarily combine the protector, sensor array and first joint trial into an assembly for use.

17. The modified system of claim 12 wherein the articulating surfaces of the first joint trial and the protector are concave and the articulating surface of the second joint trial is convex and wherein the mating members are spaced from the concave articulating surfaces of the first joint trial and the articulating surface of the protector.

18. The modified system of claim 17 wherein the first joint trial includes an additional surface adjacent to the concave articulating surface of the first joint trial and wherein one of the mating members is associated with the additional surface of the first joint trial.

19. The modified system of claim 18 wherein the first joint trial includes a second concave articulating surface and the additional surface adjacent to the concave articulating surface is between the two articulating surfaces of the first joint trial.

20. The modified system of claim 12 wherein the articulating surfaces of the first joint trial and the protector are convex and the articulating surface of the second joint trial is concave and wherein the mating members are spaced from the articulating surfaces of the first joint trial and the protector.

21. The modified system of claim 20 wherein the first joint trial has a periphery and the protector has a periphery and the mating members are associated with the peripheries of the first joint trial and the protector.

* * * * *

UNITED STATES PATENT AND TRADEMARK OFFICE
CERTIFICATE OF CORRECTION

PATENT NO. : 7,632,283 B2 Page 1 of 1
APPLICATION NO. : 10/667685
DATED : December 15, 2009
INVENTOR(S) : Mark A. Heldreth It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 611 days.

Signed and Sealed this

Second Day of November, 2010

David J. Kappos
*Director of the United States Patent and Trademark Office*